(12) United States Patent
Griffiths et al.

(10) Patent No.: US 8,620,412 B2
(45) Date of Patent: Dec. 31, 2013

(54) APPARATUS FOR DETECTING THE POSITION OF A PERCUTANEOUSLY-INSERTED INTRAVENOUS CATHETER

(75) Inventors: Clive Griffiths, High Heaton (GB); Mike Whitaker, High Heaton (GB)

(73) Assignee: The Newcastle Upon Tyne Hospitals NHS Trust, High Heaton (GB)

( * ) Notice: Subject to any disclaimer, the term of this patent is extended or adjusted under 35 U.S.C. 154(b) by 0 days.

(21) Appl. No.: 12/597,739

(22) PCT Filed: Apr. 23, 2008

(86) PCT No.: PCT/GB2008/050282
§ 371 (c)(1),
(2), (4) Date: Feb. 2, 2010

(87) PCT Pub. No.: WO2008/129326
PCT Pub. Date: Oct. 30, 2008

(65) Prior Publication Data
US 2010/0152596 A1    Jun. 17, 2010

(30) Foreign Application Priority Data

Apr. 24, 2007   (GB) .................................. 0707906.4
Aug. 8, 2007    (GB) .................................. 0715377.8

(51) Int. Cl.
*A61B 5/0402* (2006.01)
(52) U.S. Cl.
USPC ....................................................... 600/509
(58) Field of Classification Search
USPC ....................................................... 600/509
See application file for complete search history.

(56) References Cited

U.S. PATENT DOCUMENTS

| 4,644,960 A | 2/1987 | Johans |
| 7,493,167 B2* | 2/2009 | Hussein et al. .................. 607/36 |
| 7,794,407 B2* | 9/2010 | Rothenberg .................. 600/508 |
| 2007/0225610 A1* | 9/2007 | Mickley et al. ............... 600/509 |

FOREIGN PATENT DOCUMENTS

| DE | 34 31 187 A1 | 3/1986 |
| WO | WO 2004/004596 A2 | 1/2004 |

OTHER PUBLICATIONS

Tsui et al. Umbilical vein catheterization under electrocardiogram guidance. Pediatric Anesthesia. 15:4 (2005)].*

* cited by examiner

*Primary Examiner* — Christopher D Koharski
*Assistant Examiner* — Jeremiah Kimball
(74) *Attorney, Agent, or Firm* — Kinney & Lange, P.A.

(57) ABSTRACT

An apparatus that is able to detect the position of a catheter. The apparatus utilizes a catheter filled with electrically-conductive physiological saline and a connector for establishing an electrical connection between the saline of the catheter and an input of a controller. The controller includes at least one output connectable to a standard ECG lead connector, wherein the controller includes circuitry for generating a low impedance output signal. The controller provides an output which replicates the input a standard ECG patient lead connector is configured to receive. The apparatus provides a more convenient and cost effective solution for providing specialized ECG functions without having to replace a hospital's existing ECG beside monitoring equipment.

16 Claims, 4 Drawing Sheets

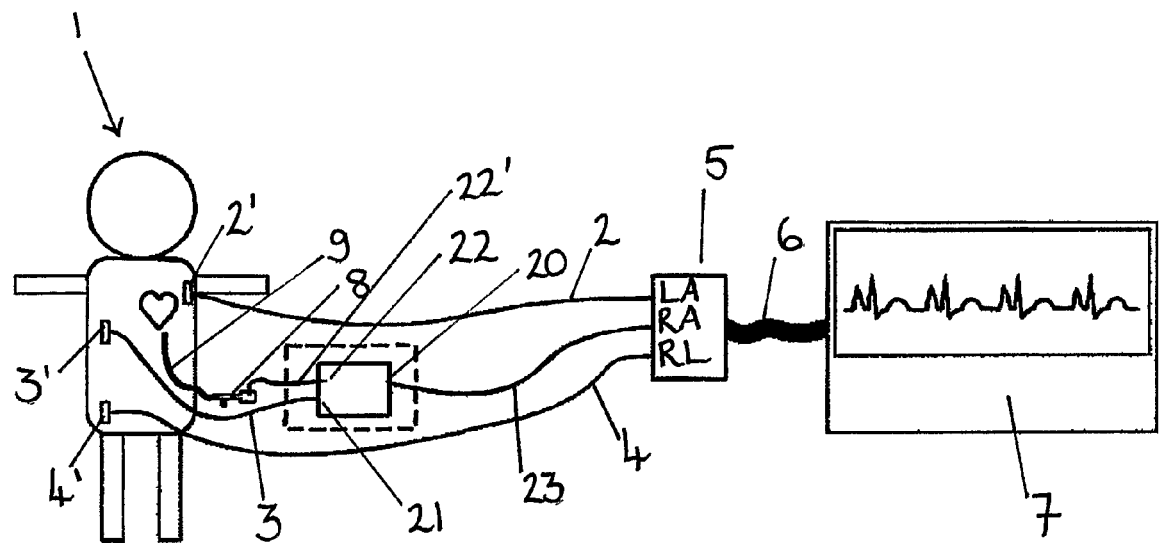
FIGURE 4a
FIGURE 4b
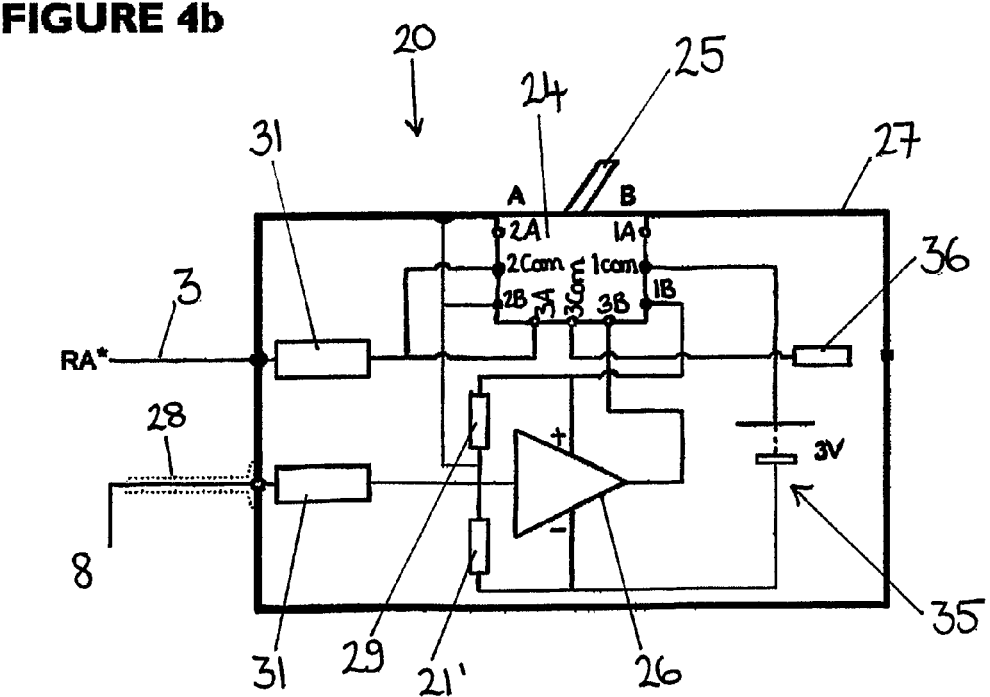

APPARATUS FOR DETECTING THE POSITION OF A PERCUTANEOUSLY-INSERTED INTRAVENOUS CATHETER

FIELD OF THE INVENTION

The present invention relates to an apparatus for detecting the position of a percutaneously-inserted intravenous catheter and in particular to such an apparatus for use in neonates and in adults when a catheter is required to be positioned close to the heart.

BACKGROUND OF THE INVENTION

Percutaneously-inserted intravenous catheters are used in neonates for a number of reasons including parenteral nutrition, infusing drugs and taking blood for example. When carrying out such procedures the end of the catheter is inserted into a vein and positioned in close proximity to the heart in the vena cava. In some procedures performed shortly after birth, an umbilical vein is used.

The current procedure for inserting a catheter uses a catheter marked with graduations. To insert the catheter marked with graduations into a neonate involves measuring the baby and applying a formula to determine to which graduation the catheter should be inserted and then taking X-ray images of the baby to check the position of the catheter. If the catheter has been inserted too far it can be withdrawn slightly. However, if the catheter has not been inserted sufficiently far it cannot be inserted further due to loss of the sterile insertion field when performing the X-ray.

Using a procedure which involves taking X-ray images of a neonate is not desirable for a number of reasons. First, exposure to X-rays can itself lead to harm. Secondly, it is necessary to disturb or move the neonate from one location to another to perform the X-ray. Such movement of an ill neonate can cause distress leading to clinical deterioration, and also may involve delay. Thirdly, the very fine gauge intravenous lines used in neonatal practice may be difficult to localise accurately on X-ray, even with the use of contrast media.

Another known procedure involves making a catheter one of the electrodes of an electrocardiogram (referred to hereinafter as an "ECG") monitor by filling the catheter with electrically conductive saline and attaching a Vygon® connector or similar to the catheter. The idea behind the Vygon® connector is that with the catheter acting as an electrode, as it moves to the correct position with respect to the baby's heart a characteristic pattern is produced on the display of the ECG. Such a procedure is described in a number of academic papers. For example: Ban C. H. Tsui et al, Umbilical vein catheterization under electrocardiogram guidance, Pediatric Anesthesia 2005, 15: 297-300; Hoffman M. A. et al, Central Venous Catheters No X-Rays Needed: A Prospective Study in 50 Consecutive Infants and Children, Journal of Pediatric Surgery, Vol 23, No 12 (December), 1988: pp 1201-1203; Neubauer A-P, Percutaneous central iv access in the neonate: experience with 535 silastic catheters, Acta Paediatr 84: 756-60. 1995; Neubauer A-P, Central Venous Placement of Silastic Catheters by Recording the Intravascular ECG A Prospective Study in 50 Infants Weighing Less than 1000 g, Klin Padiatr 1991, 203: 146-148.

In Hoffman M. A. et al, Central Venous Catheters No X-Rays Needed: A Prospective Study in 50 Consecutive Infants and Children, Journal of Pediatric Surgery, Vol 23, No 12 (December), 1988: pp 1201-1203, central veneous catheterization was performed on infants and children using catheters having internal diameters of 0.025 to 0.040 inches (0.635 mm to 1.016 mm). The catheter was first flushed with 0.9% saline and then filled with 3% saline. An electrical connection was made from the distal end of the catheter to the operating room oscilloscope, replacing the left arm input lead.

In Ban C. H. Tsui et al, Umbilical vein catheterization under electrocardiogram guidance, Pediatric Anesthesia 2005, 15: 297-300, umbilical venous catheters (referred to hereinafter as "UVC") were inserted from the umbilicus into the thorax, with the optimal position being when the catheter tip was located in the inferior vena cava or at the junction of the inferior vena cava (referred to hereinafter "IVC") and the right atrium. These experimenters connected a Johans ECG adapter to the distal port of a 3 or 5 French (single or triple lumen) UVC so that the tip of the UVC would become a unipolar ECG electrode. The (external) diameter of a 3 French UVC is 1.00 mm whereas the (external) diameter of a 5 French UVC is 1.7 mm.

In Neubauer A-P, Percutaneous central access in the neonate: experience with 535 silastic catheters, Acta Paediatr 84: 756-60. 1995 the catheters used were Epicutaneo Cava-Catheters (Art. No 2184.005, Vygon Medical Products Aachen, Germany) having a length of 30 cm, an internal diameter of 0.3 mm and an external diameter of 0.6 mm. The catheter was filled with 5.85% NaCl solution.

A problem associated with using the connectors of the Vygon® type is that noise arising from interference, typically mains interference and movement artifacts, prevents an accurate pattern being determined. Excessive noise is produced due to the very high impedance of electrically conductive saline resulting from the very small diameter of the catheter. Neubauer recognized that by increasing the conductive capacity of the saline, this problem could be reduced. He states that through the use of a catheter filled with conducting solution the percentage of radiologically diagnosed malpositions decreased from 64.5% to 9.5%. Furthermore, the interpretation of the ECG tracing presented no difficulty even to the less experienced operator. However, increasing the strength of the saline solution can damage the red blood cells and carries risk of hypernatremia.

In A P Neubauer, Die zentralvenöse Plazierunf des Silastikkatheters durch Ableitung eines intravasalen EKG Eine prospective Untersuchung an 50 Frühgeborenen unter 1000 g, Klin Padiatr, 203 (1991), it is recognized that when small diameter catheters, which must be used in neonates, are connected to an ECG, the output signal is subject to a significant amount of interference when the catheter is filled with physiological saline. Neubauer overcomes this problem by increasing the conductivity of the saline solution, which is achieved by using 5.85% saline solution. Neubauer recognizes that over-supplying sodium and chloride can be harmful to neonates and overcomes this in the smallest of children by first filling the catheter with glucose solution which may be sprayed out of the catheter without any risk in the event of difficulty in inserting the catheter being encountered. The catheter is only filled with 5.85% saline solution just before the desired insertion length is reached.

In neonates it is desirable to use catheters having very small diameters, both external and internal. As recognized by Neubauer, when filled with physiological saline the impedance of such catheters is very high and the electrical signal detected by such a catheter is accompanied by a great deal of noise due to this high impedance.

In each of the above-mentioned academic papers either the catheter is of a substantial diameter when compared to the diameter of catheter used intravenously in a neonate and/or a more conductive rather than physiological saline solution is used when positioning the catheter. In both circumstances the impedance of the saline within the catheter is reduced when compared with the impedance arising when using a catheter of the diameter suitable for intravenous use in a neonate with physiological saline.

The aim of the invention is to allow the catheter to be used as an electrode of an ECG and to produce a signal which is substantially free of noise and which uses physiological saline.

SUMMARY OF THE INVENTION

According to the invention there is provided an apparatus for detecting the position of a catheter comprising a catheter, electrically conductive means associated with the catheter, a connector for establishing an electrical connection between the electrically conductive means associated with the catheter and an output of the connector and a controller having at least one output connectable to an ECG patient connector, wherein the controller includes at least one input and the said at least one input includes an electrical connection from the controller to the output of the connector and wherein the controller includes means for generating a low impedance output signal.

Preferably the means to generate a low impedance output signal includes at least one operational amplifier, at least one of which may be configured as a buffer.

Advantageously, the electrically conductive means is physiological saline.

Preferably the controller includes two inputs; one of the inputs is connected to the output of the connector and the other input is connected to one of the right arm (RA), left arm (LA) and right leg (RL) electrodes. The controller may include a switch to provide for switching the output of the controller between the catheter and the one of the RA, LA & RL signals. An operational amplifier of the controller may be provided with a reference voltage derived from the detected RA signal.

In one embodiment of the invention one of the at least one operational amplifiers is a differential amplifier. The apparatus may further include an inverting amplifier, which is advantageously connected to a right leg (RL) input to the controller.

Attachment of the controller input to the catheter connector may be located substantially adjacent to the catheter connector, and may be incorporated into said connector. Alternatively, the controller may be located at a distance from the said connector and an electrical connector may be provided between the two components.

The electrical connection between the catheter connector and the controller may be provided with a shield, to shield said electrical connection against electrical interference.

One type of catheter connector is a Vygon® connector. However, any connector capable of providing an electrical connection to the electrically conductive media associated with the catheter and connection means for connection to other electrical devices may be used.

Advantageously, the controller is housed in a case and the inner surface of the case is provided with an electrical conductor.

The catheter is preferably of the type for insertion in a vein, which may be a vein of the umbilical cord. The size of the catheter is desirably in the range suitable for insertion into a neonate.

The invention also relates to a method of detecting the position of a catheter, using apparatus according to the invention, inserting the catheter in a patient and watching for an output on the ECG screen representative of a desired position.

BRIEF DESCRIPTION OF THE DRAWINGS

In the drawings, which illustrate a preferred embodiment of the invention, and are by way of example:

FIG. 3b is a circuit diagram of a component of the apparatus illustrated in FIG. 3a;

FIG. 4a is a schematic representation of an apparatus according to another embodiment of the invention;

FIG. 4b is a circuit diagram of a component of the apparatus illustrated in FIG. 4a.

DETAILED DESCRIPTION OF THE PREFERRED EMBODIMENT

The ensuing description assumes that the ECG monitor is configured as ECG Lead I (left arm-right arm) (Einthoven system) using right leg as reference. Other lead configurations are equally possible, such as configurations in which the left leg is used as a reference.

Figure 1:
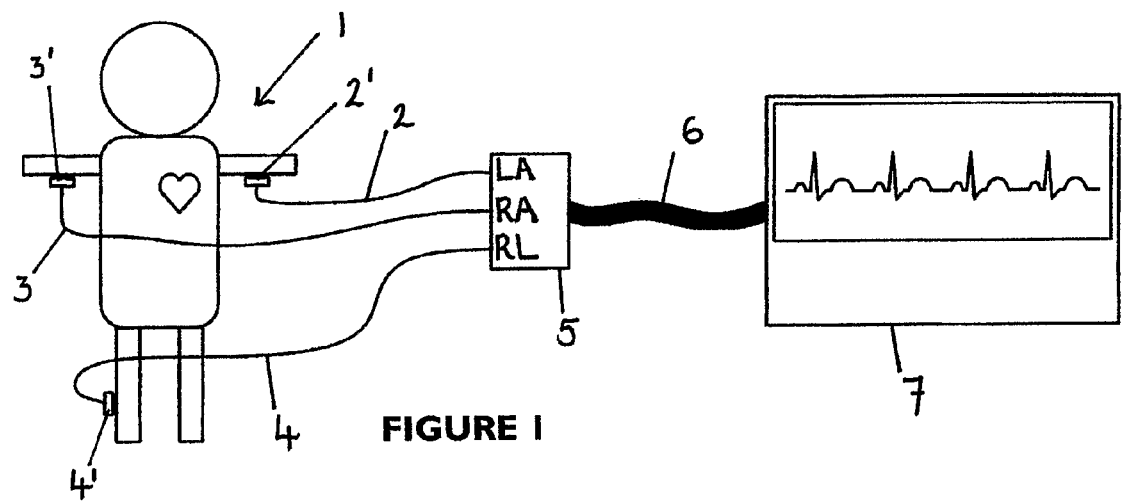
FIG. 1 is a schematic representation of a standard electrocardiogram (ECG)

Referring now to FIG. 1, there is shown a typical arrangement of an ECG on an individual 1 in which leads 2, 3 and 4 are connected to the left arm, right arm and right leg respectively by electrodes 2', 3' and 4'. The leads 2 to 4 are connected respectively to the left arm (LA), right arm (RA) and right leg (RL) terminals on a patient lead connector 5, which is itself connected to by a cable 6 to an ECG monitor 7. Interference is not a significant problem with this arrangement as each of the leads 2 to 4 presents substantially the same, relatively low impedance.

Figure 2:
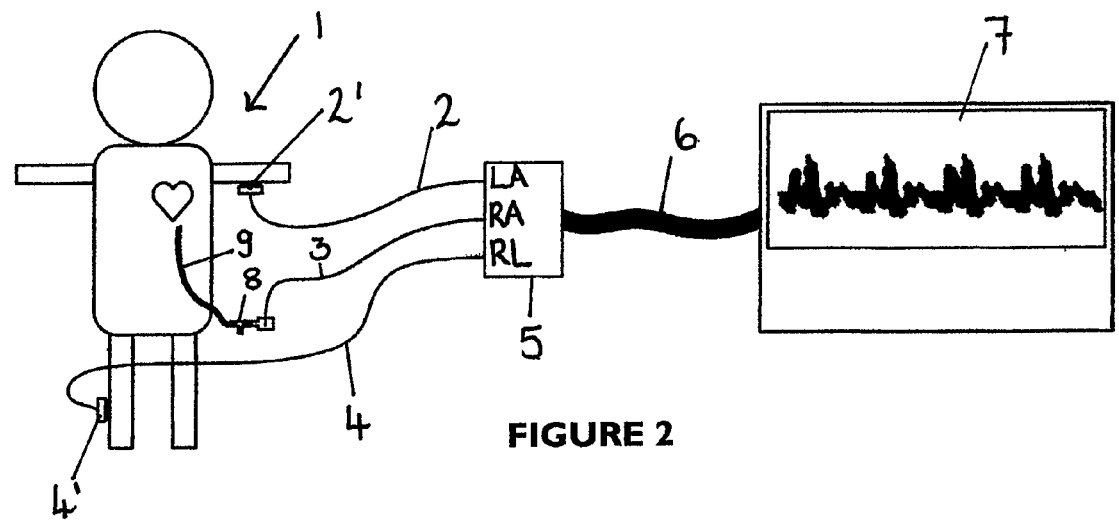
FIG. 2 is a schematic representation of an ECG having its RA connection attached to a Vygon connector.

Referring now to FIG. 2, where the individual 1 is a neonate, instead of the lead 3 which connects to the RA terminal of the patient lead connector being attached to a electrode 3' which is itself attached to the arm of the individual 1, as is illustrated in FIG. 1, the lead 2 is connected to a Vygon® connector 8. The Vygon® connector allows a catheter 9 which is filled with a conductive solution of physiological saline to be connected to the patient lead connector 5. In the illustrated example the catheter 9 replaces the right arm RA connection 3' to the individual 1. As can be seen, the trace on the ECG monitor 7 exhibits significant noise when compared to the trace illustrated in FIG. 1. This phenomenon was noticed by Neubauer (see above) and is due to the impedance of the saline solution in the catheter 9 which has a very small internal diameter due to the diameter of neonate veins into which the catheter must be inserted.

Interference is principally due to electric fields surrounding mains electric cabling and electric fields emanating from mains electricity consuming devices present in the environment where the ECG is to be used and also movement artifacts which are accentuated by the high impedance of the catheter. In the case of a standard ECG such interference is of no consequence as the resistance of the leads RA, LA and RL are substantially the same and are relatively low therefore any induced voltages are small and tend to cancel each other out.

Where the impedance of one lead is markedly different to that of another the induced voltages are different and cannot cancel one another out.

Figure 3A:
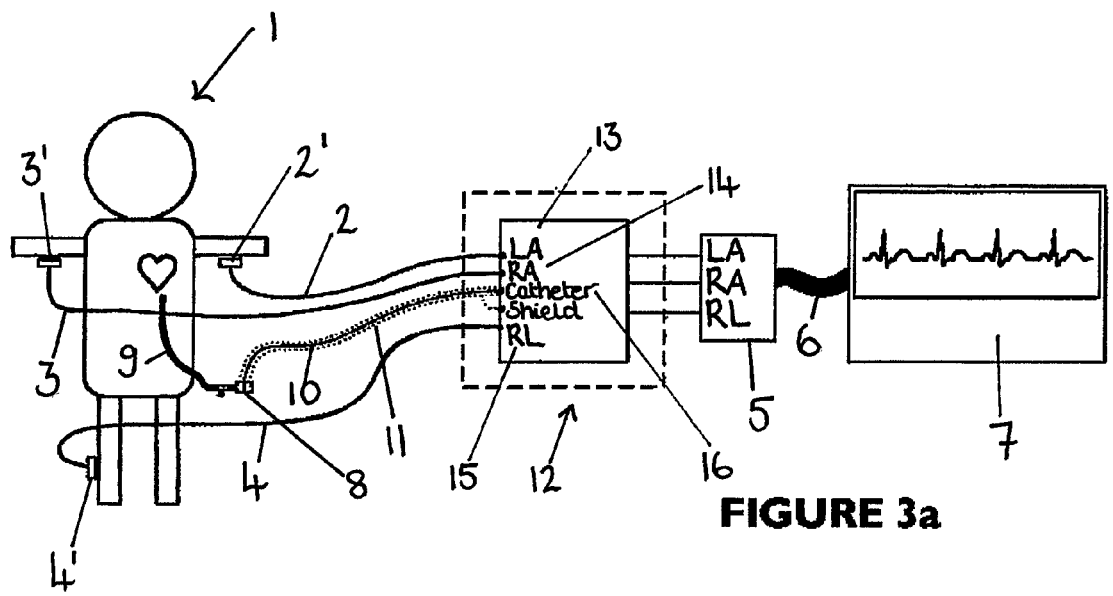
FIG. 3a is a schematic representation of an apparatus according to one embodiment of the invention.
Figure 3B:
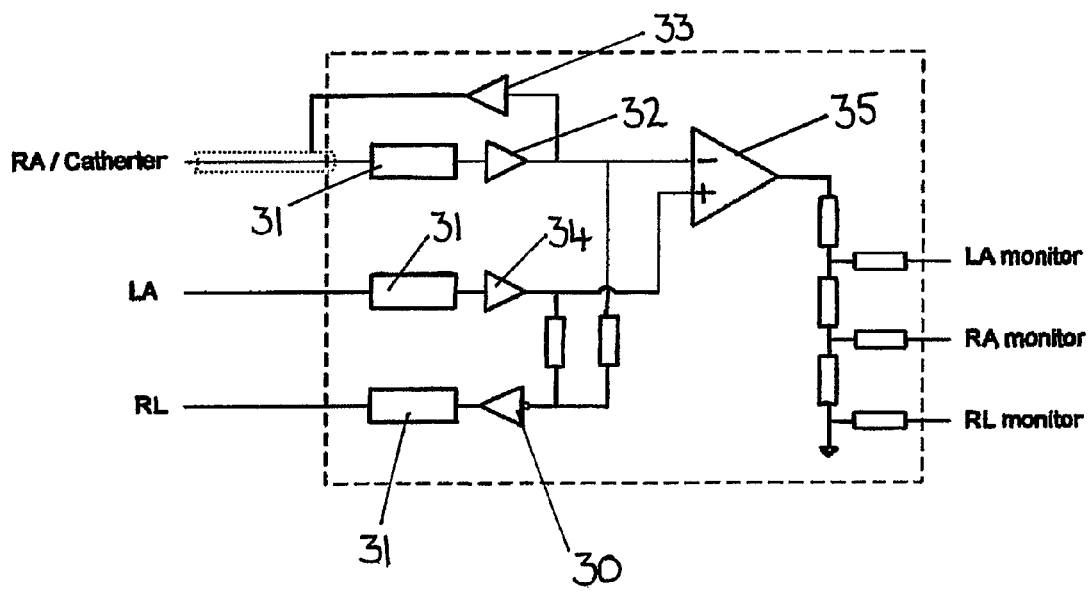

Referring now to FIGS. 3a and 3b, an apparatus is illustrated comprising leads 2, 3, 4 each having a respective electrode 2', 3' and 4' for attachment to a patient 1. The leads 2, 3 and 4 are attached to a standard ECG patient connector 5 by means of a controller 12, which itself is provided with input ports 13 to 16 for the connection of the lead 2 which is attached to the left arm (LA), the lead 3 which is attached to the right arm (RA), and the lead 4 which is attached to the right leg (RL). The input port 16 of the controller 12 is provided to allow a catheter 9, which is filled with physiological saline (that is 0.9% saline solution) to be connected to the controller 12 using a connector 8, which in the present example is a Vygon® connector. A lead 10 extends between and is attached to the connector 8 and the port 16 of the controller 12. The lead 10 is provided with a shield 11 which reduces the effect of electrical interference from mains circuits within the environment in which the apparatus is being operated on the signal produced by the catheter. The shield may or may not be required depending on the noise level of the particular environment, and the length of the lead 10.

The controller 12 is designed to provide outputs which replicate substantially the inputs an ECG monitor expects to receive. To this end a reference voltage is provided by the connection to the right leg. Even with such a reference connection the controller can be affected by what is known as the common mode signal, which is noise arising from voltages generated within the patient. In order to reduce the effects of the common mode signal the controller 12 includes an inverting amplifier 30. This ensures that the reference voltage of the controller 12 is at zero volts relative to the patient. Without the inverting amplifier 30 the RL input to the ECG monitor would be zero volts and the reference voltage of the controller 12 would be at the common mode voltage.

Each of the RA/catheter, LA and RL inputs to the controller 12 is provided with radio frequency protective circuitry 31. Such circuitry 31 is required as interference from radio frequency signals can demodulate to have a frequency which is in the area of interest when using an ECG on a patient.

The circuit includes buffers 32 and 33 associated with the RA/Catheter input signals to the controller 12 and a buffer 34 associated with the LA input to the controller 12. Buffer 33 feeds back to the catheter shield 11.

The function of the buffers 32 to 34 is to convert a high impedance input to a low impedance output.

The respective outputs of the buffers 32 and 34, and the output of the inverting amplifier form inputs to a differential amplifier 35. The output of the differential amplifier is the desired signal, as the output thereof represents the voltage detected at the tip of the catheter 9. However, the ECG needs to receive input signals in the form of RL, RA and LA input signals. The output of the differential amplifier 35 is therefore split into signals which appear to the ECG patient connector 5 as the signals that might be received from three patient connections RA, LA and RL.

An alternative embodiment of the invention is illustrated in FIGS. 4a and 4b.

Leads 2 and 4 connect the LA and RL ports of a patient ECG connector 5 to a patient 1 by means of connection electrodes 2' and 4' respectively. A controller 20 is located between the patient 1 and the patient ECG connector 5. The output of the controller 20 is connected to the RA port of the patient ECG connector 5 by a lead 23. The controller 20 has two input ports 21 and 22. Input 21 is an RA port and is connected by a lead 3 to the electrode 3'. One end of a lead 22' is connected to the port 22, with the other end of the lead being attached to a connector 8 (which in the present example is a Vygon® connector), which is attached to a catheter 9. In use, the catheter 9 is filled with physiological saline, i.e. 0.9% saline.

Referring now to FIG. 4b, the internal architecture of the controller 20 is illustrated. The controller 20 includes a switch 24 operated by a toggle 25. The device may be switched such that the input to the controller 20 is either from the catheter 9 or an electrode otherwise attached to the body, which in the present example this is the electrode 3' which is attached by lead 3 to the RA input of the controller 20.

When the toggle 25 is in position A the battery, screening and all active components are disconnected from the RA input which is connected directly by the switch 24 to the output, i.e. port 3A is connected to port 3Com, which is connected by lead 23 to the RA input of the patient ECG connector 5.

When the toggle 25 is in position B, the case screen 27 and catheter connection screen 28 are each connected to the RA lead 3 which is connected to the patient 1. In this configuration the RA connection to the patient provides a reference voltage for the buffer 26 which in this embodiment is split by resistors 29 and 29' to provide voltages of +1.5V and −1.5V either side of the reference voltage to each side of the buffer 26, but other arrangements are possible. The patient voltage can change by more than the supply voltage of 3 volts (provided by battery 35). Without referencing the supply voltage to the patient it is conceivable that the patient voltage may change by more than the supply voltage of 3 volts. By referencing the supply voltage to the patient voltage, the supply voltage effectively follows the patient voltage and the problem is removed.

The position of the toggle 25 of switch 24 determines the path through which electrical current flows. When set to position A, the ports labeled 1A, 2A and 3A are connected to the ports 1 Com, 2 Com, 3 Com. When set to position B, the ports labeled 1B, 2B and 3B are connected to the ports 1 Com, 2 Com, and 3 Com.

The invention utilizes one of the properties of an operational amplifier, i.e. to convert a high impedance input into a low impedance output. The buffer 26 does this. With the toggle in position B, the output of the buffer 26, which is connected to port 3B is connected to port 3 Com, which in turn is connected to a resistor 36 and the RA input of the ECG patient connector 5.

The present invention allows very small diameter catheters to be inserted into very small children without the use of X-rays. Further, the present invention provides for the insertion of such a catheter when the catheter is filled only with physiological saline. Whilst other researchers have noted the problem addressed by the present invention, none have arrived at the solution now proposed. Earlier research relies on reducing the impedance of the saline by increasing its strength. The researchers take steps to avoid the problems associated with concentrated saline solutions.

The arrangement shown in FIGS. 4a and 4b is particularly simple, and may be miniaturised such that it may attach directly to the end of the connector 8, or be an integral part thereof. Further, use of the device is particularly simple. All that is required is for a member of medical staff to connect the lead 23 from RA connection of the patient connector 5 to the output port of the controller 20. The output of the controller can be switched between RA and catheter as the medical staff wish.

Figure 4C:
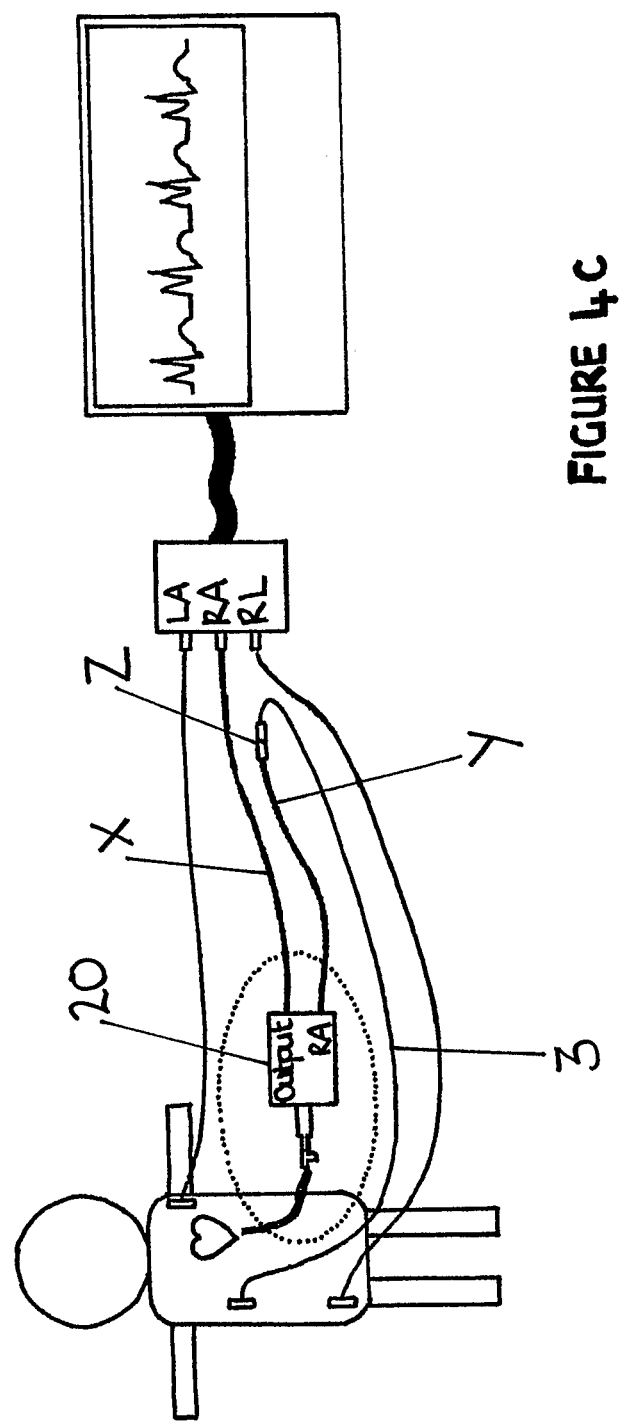
FIG. 4c is schematic representation of apparatus according to another embodiment of the invention.

In FIG. 4c, which illustrates a further embodiment of the invention, components common to the embodiments illustrated in FIGS. 4a, b and c are indicated by common reference numerals.

In the apparatus of the embodiment illustrated in FIG. 4c, the controller 20 is battery powered and once activated is permanently on, until the battery runs dry. The controller 20 is provided with a plastic tab which pulls out of the battery connection when the controller 20 is to be used for the first time. Once removed the controller 20 is powered. Such an arrangement, when compared to an arrangement including an on/off switch is significantly less bulky. This is because the switch would need to be electrically insulated to a high level to comply with current safety standards.

The apparatus illustrated in FIG. 4c differs in the arrangement of the right arm electrode between the controller 20 and the patient. In FIG. 4a, the lead 3 is connected directly from the right arm electrode to the controller. However this brings lead 3 which is potentially not sterile into what should be a sterile zone.

The aforementioned problem is solved by the arrangement illustrated in FIG. 4c, where two sterile leads X and Y are utilised. When supplied to an end user, such as a hospital, the sterile leads X and Y are already attached to the sterile controller 20. The apparatus of FIG. 4c includes an additional connector Z, which is attached to the end of sterile lead Y. The lead 3 which goes to the right arm electrode of the patient connects to the sterile lead Y via this connector Z. In this way, the lead 3 need not enter the sterile zone 37 in the first place, and so it does not have to be sterile.

In the embodiment illustrated in FIG. 4c the connector 8 is attached directly to the controller 20.

In another embodiment, the switch 24 is not fitted. This will facilitate a very low cost, single-use version of the device.

The invention claimed is:

1. Catheter position detection apparatus for detecting the position of a catheter in a neonate with respect to the neonate's heart, comprising:
    electrically conductive means associated with the catheter,
    a connector for establishing an electrical connection between the electrically conductive means associated with the catheter and an output of the connector; and
    a controller having at least one output connectable to a separate ECG patient connector,
    wherein the controller includes at least one first input including an electrical connection from the controller to the output of the connector,
    wherein the controller includes means for generating a low impedance output signal,
    wherein the controller provides at least one output which replicates the input a standard ECG patient connector is configured to receive, and
    wherein the controller includes at least one second input connected to a body electrode attachable to a part of the patient's body, wherein the second input connected to the body electrode is provided with an electrical connector located between the controller and the body electrode, and wherein the electrical connector located between the controller and the body electrode is located, in use, outside a sterile zone.

2. Apparatus according to claim 1, wherein the means to generate a low impedance output signal includes at least one operational amplifier.

3. Apparatus according to claim 2, wherein the at least one operational amplifier is configured as a buffer.

4. Apparatus according to claim 1, wherein the electrically conductive means is physiological saline.

5. Apparatus according to claim 1, wherein the body electrode is selected from the group consisting of: right arm (RA), left arm (LA) and right leg (RL) electrodes.

6. Apparatus according to claim 1, wherein the controller includes a switch to provide for switching the output of the controller between the catheter and the signal derived from a body electrode.

7. Apparatus according to claim 2, wherein one of the at least one operational amplifiers is provided with a reference voltage derived from a signal derived from a body electrode.

8. Apparatus according to claim 7, wherein one of the at least one operational amplifiers is a differential amplifier.

9. Apparatus according to claim 1, wherein the apparatus further includes an inverting amplifier.

10. Apparatus according to claim 9, wherein the inverting amplifier is connected to a body electrode input to the controller.

11. Apparatus according to claim 1, further comprising attachment means for attachment of the controller input to the catheter connector, and wherein the attachment means is located substantially adjacent the catheter connector.

12. Apparatus according to claim 11, wherein the attachment means for attachment of the controller input to the catheter connector is incorporated into said catheter connector.

13. Apparatus according to claim 1, wherein the electrical connection between the catheter connector and the controller is provided with a shield to shield said electrical connection against electrical interference.

14. Apparatus according to claim 1, wherein the controller is housed in a case and the inner surface of the case is provided with an electrical conductor.

15. Apparatus according to claim 1, wherein an internal diameter of the catheter is in the range 0.1 mm to 3.0 mm.

16. A method of detecting the position of a catheter, using the apparatus of claim 1, comprising the steps of:
    i. inserting the catheter into a vein of a patient;
    ii. observing an output on an ECG screen; and
    iii. ceasing insertion of the catheter when the output on the ECG screen representative of a desired position of the catheter is observed.

* * * * *